United States Patent [19]

Uematsu et al.

[11] Patent Number: 4,877,492
[45] Date of Patent: Oct. 31, 1989

[54] METHOD OF MEASURING ELECTROLYTE IN BLOOD AND URINE BY ELECTRODE METHOD

[75] Inventors: Hiroaki Uematsu; Shinji Imanishi, both of Kyoto, Japan

[73] Assignee: Horiba, Ltd., Kyoto, Japan

[21] Appl. No.: 204,994

[22] Filed: Jun. 10, 1988

Related U.S. Application Data

[63] Continuation of Ser. No. 948,064, Dec. 30, 1986, abandoned.

[30] Foreign Application Priority Data

Jan. 11, 1986 [JP] Japan .................................. 61-3800

[51] Int. Cl.[4] ..................... G01N 27/26; G01N 33/20; G01N 33/49; G01N 33/493
[52] U.S. Cl. ..................................... 204/1 T; 436/79; 436/179; 436/124; 436/125
[58] Field of Search ............... 204/1 T, 1 A, 403, 416; 436/74, 79, 179, 124, 125

[56] References Cited

U.S. PATENT DOCUMENTS 4,416,735  11/1983  Kissel .................................. 204/1 T

FOREIGN PATENT DOCUMENTS 132210    9/1978  Fed. Rep. of Germany ...... 204/1 T
59-192954 11/1984 Japan ................................ 204/1 T Primary Examiner—John F. Niebling
Assistant Examiner—Ben C. Hsing
Attorney, Agent, or Firm—Wenderoth, Lind & Ponack

[57] ABSTRACT

Method of measuring electrolyte concentration in a urine sample, by preparing a calibrating solution containing ions of the electrolytes to be measured, preparing a diluent containing the same ions, diluting the urine sample with the diluent, measuring the electrolyte in the diluted urine with an electrode using the calibrating solution, and calculating the concentration of electrolyte based on the measured value. Additionally, the concentration of the same electrolytes in a blood sample can be measured without dilution, using the same calibrating solution.

3 Claims, 11 Drawing Sheets

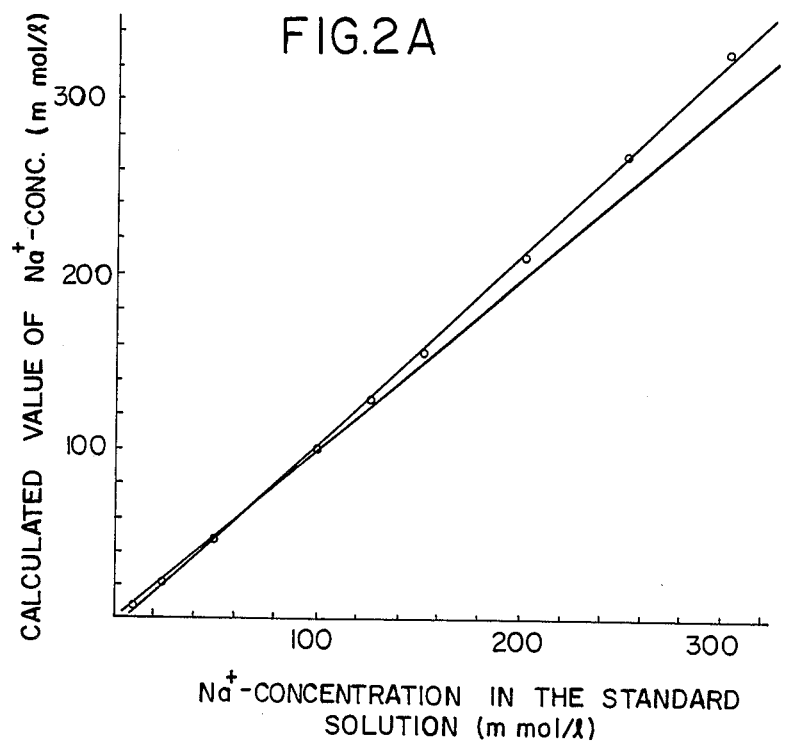
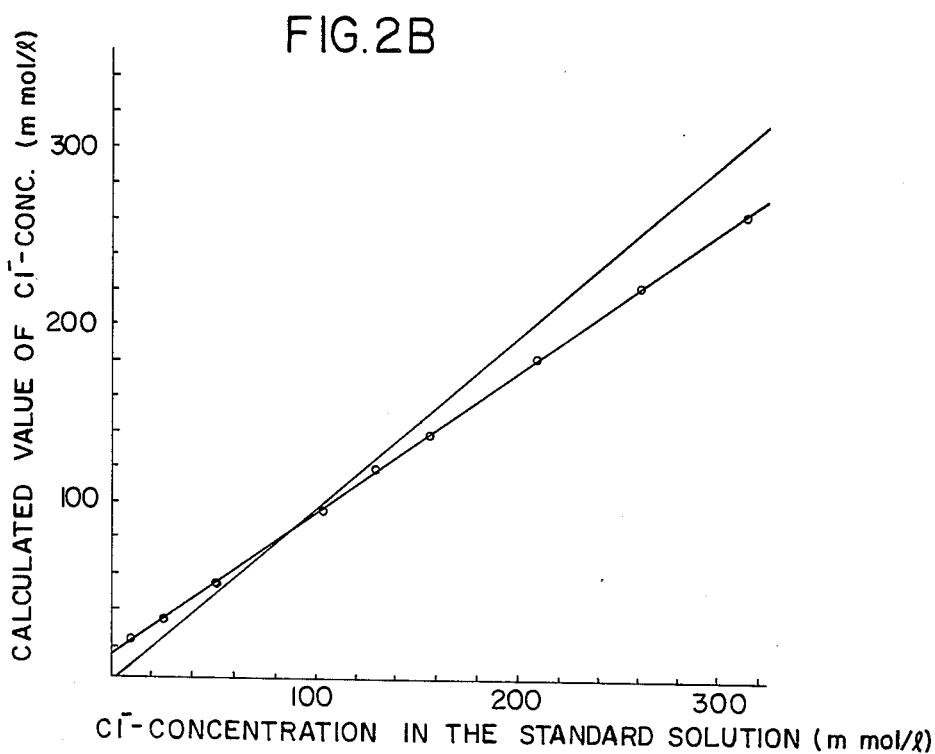

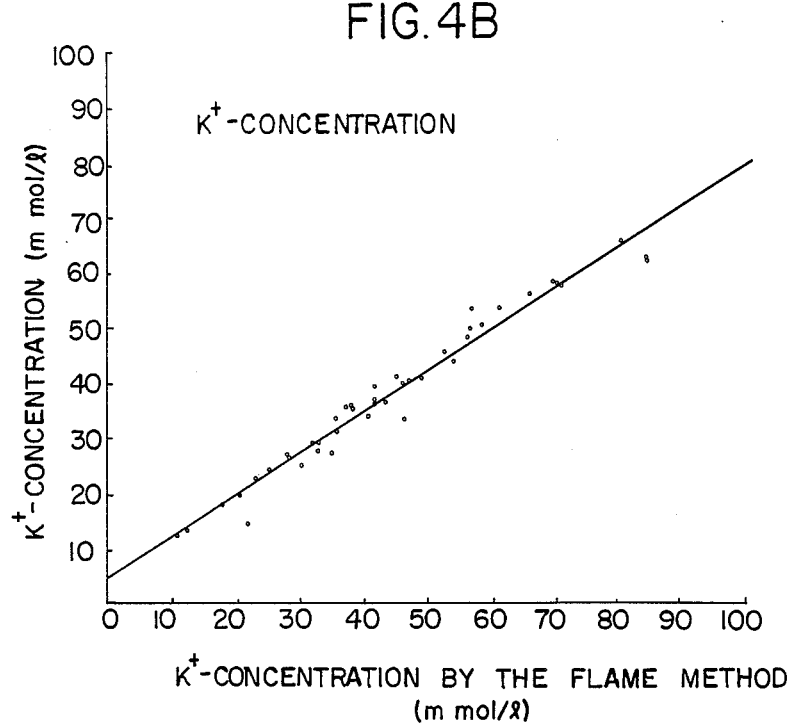
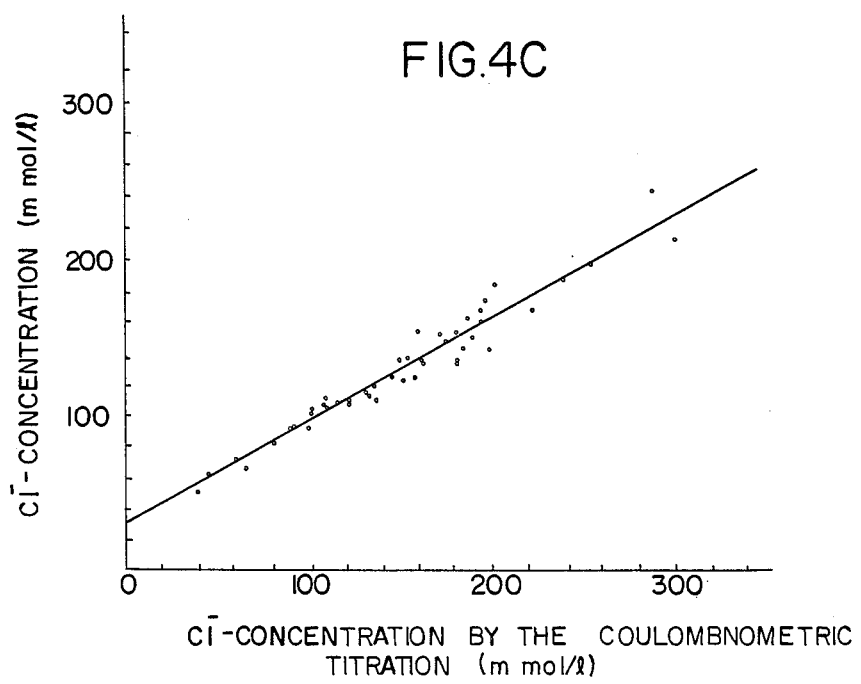

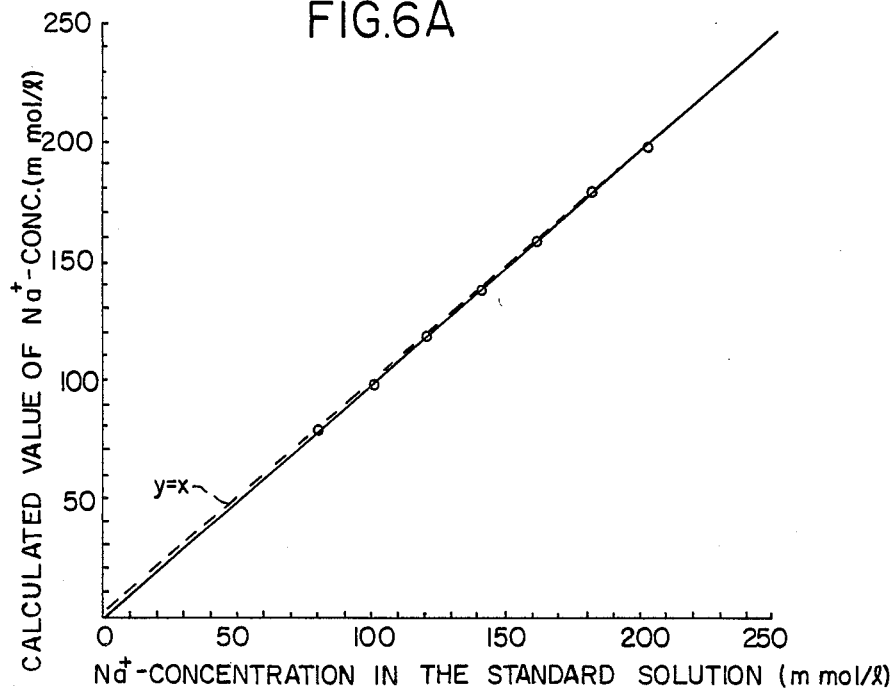
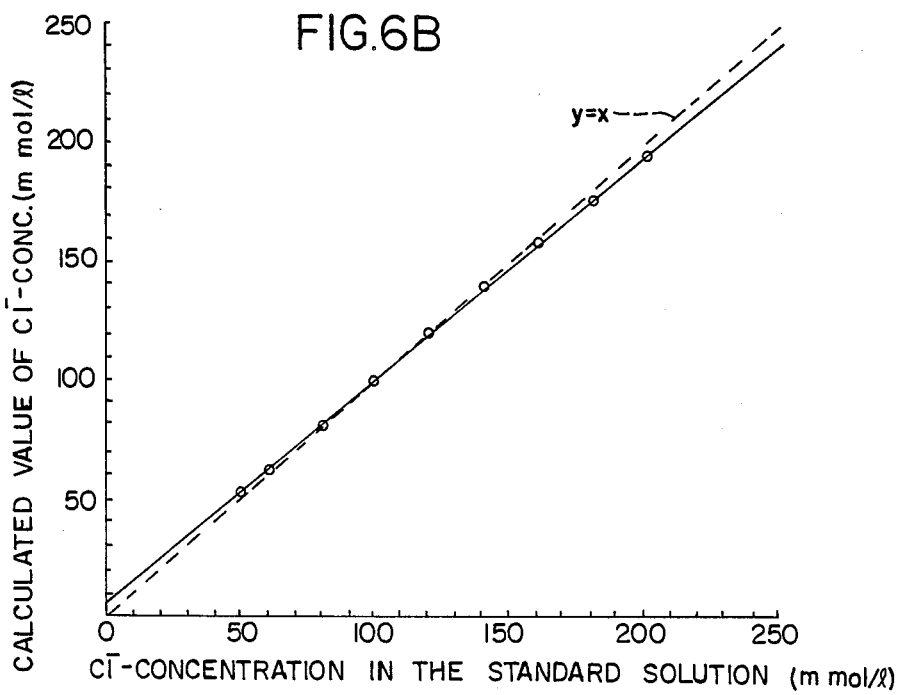

METHOD OF MEASURING ELECTROLYTE IN BLOOD AND URINE BY ELECTRODE METHOD

This application is a continuation of now abandoned application Ser. No. 948,064 filed Dec. 30, 1986 now abandoned.

BACKGROUND OF THE INVENTION

1. Field of the Invention

The present invention relates to a method of measuring electrolytes in blood and urine by use of an electrode.

2. Description of the Prior Art

In case where electrolytes in a blood and urine are measured by use of an electrode, the measuring range is as follows for a blood:

| | |
|---|---|
| $Na^+$-concentration | 100 to 200 mmol/liter |
| $K^+$-concentration | 1.0 to 10.0 mmol/liter |
| $Cl^-$-concentration | 80 to 200 mmol/liter |

On the contrary, for a urine the measuring range is as follows:

| | |
|---|---|
| $Na^+$-concentration | 2 to 300 mmol/liter |
| $K^+$-concentration | 1 to 150 mmol/liter |
| $Cl^-$-concentration | 2 to 300 mmol/liter |

That is to say, the measuring range for a urine is considerably wide in comparison with that for a blood. A reason for this is that the metabolism of electrolytes is carried out in a remarkably narrow range for a blood and a slightest change of concentration exhibits a physiological activity while for a urine a quantity of salts and water ingested is directly reflected in the quantity thereof excreted, thereby remarkably changing the concentration of electrolytes.

Accordingly, in a case where a blood and a urine are measured in an apparatus for measuring electrolytes by use of an electrode, calibrating solutions (Low standard solution, High standard solution) for a blood and a urine are separately prepared and calibrating points for the calibrating solution for a blood are determined in the measuring range for a blood, thereby improving the accuracy in the measurement of a blood, while calibrating points for the calibrating solution for a urine are widely taken, thereby taking a measurement in as wide a range as possible. In this case, for example the following two kinds of calibrating solution have been used:

Calibrating solutions for a blood

| | Low | High |
|---|---|---|
| $Na^+$ | 120 mmol/liter | 160 mmol/liter |
| $K^+$ | 4.0 mmol/liter | 6.0 mmol/liter |
| $Cl^-$ | 100 mmol/liter | 140 mmol/liter |

Calibrating solutions for a urine

| | Low | High |
|---|---|---|
| $Na^+$ | 80 mmol/liter | 200 mmol/liter |
| $K^+$ | 40 mmol/liter | 7 mmol/liter |
| $Cl^-$ | 80 mmol/liter | 200 mmol/liter |

In addition, it has been known that the same one calibrating solution is used in either case where the sample to be measured is a blood or a urine to carry out the measurement with a one-point calibration by taking calibrating points of the calibrating solution widely. In this measuring method for example the following calibrating solution is used:

| | Low | High |
|---|---|---|
| $Na^+$ | 130 mmol/liter | 60 mmol/liter |
| $K^+$ | 4 mmol/liter | 20 mmol/liter |
| $Cl^-$ | 116 mmol/liter | 71 mmol/liter |

Besides, in a measurement of electrolytes by the ion-electrode method the activity of electrolytes is measured, so that it is necessary for the accurate measurement of the activity that the ion-strength is constant. And, an ion-electrode itself is influenced by pH according to circumstances. Accordingly, in the measurement of a blood or a urine the ion-strength of the blood is nearly constant and also pH is in a range of 7 to 9, so that no problem occurs even though it is measured as it is. However, the urine greatly fluctuates in ion-strength and also pH is remarkably low to an extent of 4 to 6, so that it has been usually diluted with a diluent containing a buffer agent such as magnesium acetate and other support salts and a tris-boric acid system, to make the ion-strength nearly constant, and pH has been adjusted and then the measurement has been carried out.

In the above described conventional measuring method, in the case where the calibrating solution for the exclusive use of the blood and the urine is used, respectively, a high accuracy of measurement can be maintained for the blood and the urine, respectively. However, problems have occurred in that it is necessary to prepare two kinds of calibrating solution and in the case where the sample to be measured is changed from the blood to the urine, it is necessary to change the calibrating solution at the same time and to provide a measuring apparatus of an ion-electrode with a change-over valve, a line for the blood and a line for the urine, whereby the measuring apparatus is large-sized and its operation is complicated.

The measuring method in which the same one calibrating solution is used for both the blood and the urine does not require the selection of the calibrating solution depending on the sample to be measured, making it easy to prepare the calibrating solution, and being capable of simplifying the measuring apparatus in construction. However, since the calibrating points of the calibrating solution are widened because of the measuring range of the urine, problems have occurred in that the accuracy of measurement for the blood is lowered and the linearity is lost in a lower-concentration range and a higher-concentration range. That is to say the measurement is unstabilized in view of accuracy of measurement for the urine, too.

SUMMARY OF THE INVENTION

It is an object of the present invention to provide a method of measuring a blood or a urine by using an electrode which method is capable of measuring both the blood and the urine by the use of only one kind of calibrating solution, and which is capable of heightening the accuracy of measurement for both the blood and the urine.

The method according to the present invention is characterized by that as to the blood, a whole blood, a blood plasma and a serum is each used as a sample as it is, and as to a urine, a urine diluted with a diluent containing salts of ions to be measured of $Na^+$, $K^+$ and $Cl^-$ and with a buffer agent added is used as a sample, and a calibrating solution for the blood is used for the measurements of both the blood and the urine.

Ion-concentration ranges of $Na^+$, $K^+$ and $Cl^-$ to be added to the diluent for the urine in the present invention are as follows:

|       |                  |
|-------|------------------|
| $Na^+$ | 50 to 150 mmol/liter |
| $K^+$  | 0 to 4.0 mmol/liter  |
| $Cl^-$ | 50 to 150 mmol/liter |

However, in view of an ion-strength and a central value of measured values, it is desired that the concentration of $Na^+$ and $Cl^-$ is reduced to about 100 mmol/liter and the concentration of $K^+$ is reduced to 1 mmol/liter or less.

Although a tris-boric acid system and the like are preferably used as the buffer agent, any known buffer agent may be used. In addition, known support salts, such as magnesium acetate, may be added to the diluent.

The urine is diluted with the diluent at a multiplication factor of 6 to 11 to achieve the objct. But, the dilution may be carried out at a more or less multiplication factor, for example at a multiplication factor of 21 and 31. However, taking an error of dilution and like into consideration, a multiplication factor of 6 to 11 is suitable.

The calibrating solution for the blood is used as the calibrating solution, for both the blood and urine. For example, a conventional calibrating solution for the exclusive use of a blood is used.

In the measuring method according to the present invention, since the measurement of electrolytes in a blood is carried out by the use of the blood as a sample as it is, and a calibrating solution prepared for the blood is used, a highly accurate measurement can be achieved. On the other hand, in the case where a urine sample is to be measured, the calibrating solution for the blood is used as it is. Accordingly, the calibrating solution is easy to prepare and the trouble of replacement of calibrating solution and the like can be saved. And, the urine is diluted with said diluent to make an ion-strength nearly constant and simultaneously, adjusted in pH to be used as a sample to be measured. Thus, a measured value of the urine is within a range of measured values in the case where the blood is measured or adjacent to it, so that a highy accurate measured value can be obtained by the use of a calibrating solution for the blood. The calculated value of the urine is determined from this measured value.

The determination of the calculated value from said measured value of the urine is carried out by the following equations:

Calculated value of $Na^+ = n \times$ (measured value of $Na^+$) $- (n-1)x$

Calculated value of $K^+ = n \times$ (measured value of $K^+$) $- (n-1)y$

Calculated value of $Cl^- = n \times$ (measured value of $Cl^-$) $- (n-1)z$ wherein n is a multiplication factor of dilution and x, y, z is an ion-concentration of $Na^+$, $K^+$, $Cl^-$ contained in the diluent, respectively.

BRIEF DESCRIPTION OF THE DRAWINGS

FIGS. 2A, B is a graph showing a linear a relation between
$Na^+$-concentration in a urine measured by the conventional measuring method and the $Na^+$-concentration of the standard solution, and a linear a relation between
$Cl^-$-concentration in the urine measured by the conventional measuring method and the $Cl^-$-concentration of the standard solution, respectively;

FIGS. 6A, B is a graph showing a linearity of a relation between
$Na^+$-concentration in a blood measured by the conventional measuring method and a $Na^+$-concentration of the standard solution, and a linear relation between
$Cl^-$-concentration in the blood measurement by the conventional measuring method and a $Cl^-$-concentration of the standard solution, respectively.

DESCRIPTION OF THE PREFERRED EMBODIMENTS

The preferred embodiments of a method of measuring a blood and a urine according to the present invention will now be described.

A calibrating solution, which has been conventionally used for the exclusive use of a blood and has the following composition, is used for both a blood and a urine.

|       | Low           | High          |
| ----- | ------------- | ------------- |
| Na+   | 120 mmol/liter | 160 mmol/liter |
| K+    | 4.0 mmol/liter | 6.0 mmol/liter |
| Cl−   | 100 mmol/liter | 140 mmol/liter |

A diluent for the urine containing a sodium salt at an ion-concentration of 120 mmol/liter, a potassium salt at an ion-concentration of 1.0 mmol/liter and a chlorine salt at an ion-concentration of 100 mmol/liter, and having a pH adjusted with a tris-boric acid system buffer, was prepared from a solution having the following salt-concentrations:

|         | mmol/liter    |
| ------- | ------------- |
| NaCl    |               |
| KCl     | 1.0 mmol/liter |
| NaHCO3  | 21 mmol/liter |

Then the resulting diluent is used to dilute the urine at a multiplication factor of 11, thereby preparing a urine sample. The pH of this urine sample was 8.

Measured values obtained by an apparatus for measuring electrolytes by the electrode method using said urine sample and said calibrating solution for a blood are as follows:

| Na+ | 109.3 to 136.4 mmol/liter |
| K+  | 1.00 to 14.5 mmol/liter   |
| Cl− | 91.1 to 118.2 mmol/liter  |

These measured values are within said measuring ranges for a blood or adjacent to them. That is to say, it is obvious that electrolytes in the urine can be measured by the use of the calibrating solution for a blood at an accuracy equivalent to that in the case where electrolytes in the blood are measured.

The concentrations of Na+, K+ and Cl− in a urine are determined by substituting each term in each of the above equations by each measured value for the urine, that is, substituting n by 11 and x, y and z by the ion-concentration of Na+, K+ and Cl− contained in the diluent, respectively.

In addition, the electrolytes in the urine were measured with an electrode (hereinafter referred to as the conventional method) by the use of the calibrating solution prepared for both a blood and a urine for comparison.

The calibrating solution used has the following composition:

|       | Low           | High          |
| ----- | ------------- | ------------- |
| Na+   | 130 mmol/liter | 60 mmol/liter |
| K+    | 4.0 mmol/liter | 20 mmol/liter |
| Cl−   | 116 mmol/liter | 71 mmol/liter |

The diluent contains magnesium acetate as a support salt and a tris-boric acid system buffer was added. The urine was diluted at a multiplication factor of 11.

The reproducibility of the measurement for the diluted urine in the preferred embodiment (hereinafter referred to an Example) of the present invention and by the conventional method is shown in Table 1.

TABLE 1

Figure 1A:
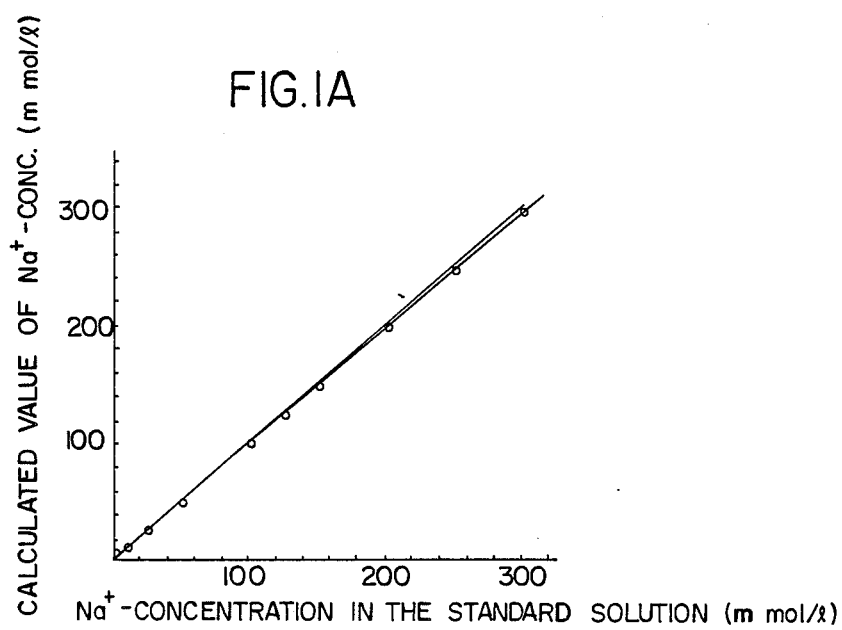
FIGS. 1A, B is a graph showing a linear relation between $Na^+$-cooncentration in a urine measured by a measuring method according to the present invention and a $Na^+$-concentration of the standard solution, and a linear a relation between $Cl^-$-concentration in the urine measured by the measuring method according to the present invention and a $Cl^-$-concentration of the standard solution, respectively.
Figure 1B:
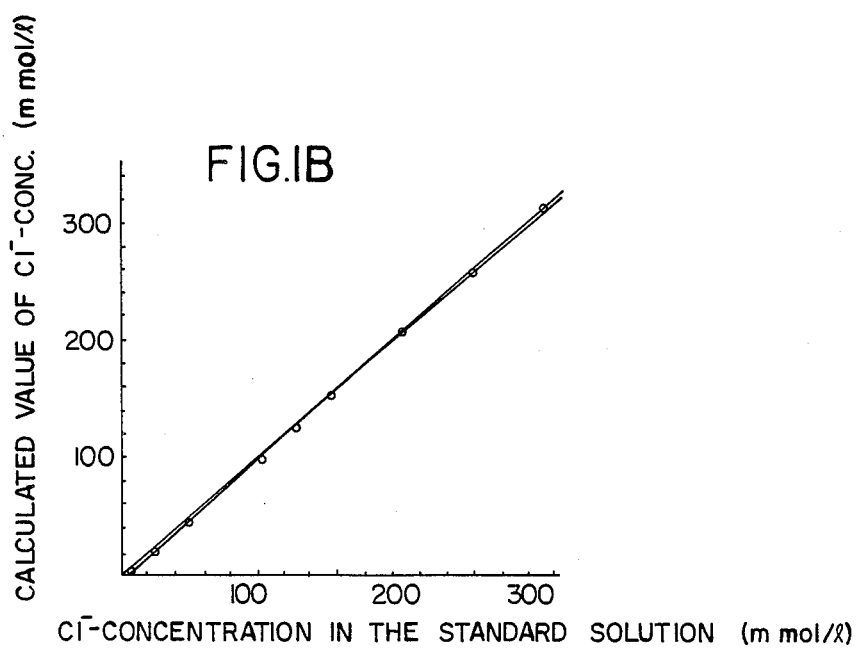

|  |  | (n = 20) | | |
| --- | --- | --- | --- | --- |
|  |  | Na+ mmol/L | K+ mmol/L | Cl− mmol/L |
| Example | x | 198.6 | 24.0 | 147.5 |
|  | S.D. | 0.72 | 0.086 | 1.00 |
|  | C.V. | 0.36% | 0.36% | 0.68% |
| Conventional method | x | 205.2 | 25.9 | 149.2 |
|  | S.D. | 2.36 | 0.732 | 5.70 |
|  | C.V. | 0.97% | 1.63% | 2.61% | wherein $\bar{x}$: average value; S.D.: standard deviation; C.V.: coefficient of variation The linear rotation between Na+-concentration in a urine measured in said Example and a Na+-concentration of the standard solution and the linear relation between Cl−-concentration in the urine measured in said Example and a Cl−-concentration of the standard solution are shown in FIGS. 1A, B. The linear relation between Na+-concentration in a urine measured by the conventional method and the Na+-concentration of the standard solution, and the linear relation between Cl−-concentration in the urine measured by the conventional method and the Cl−-concentration of the standard solution are shown in FIGS. 2A, B, C, respectively.

Figure 3A:
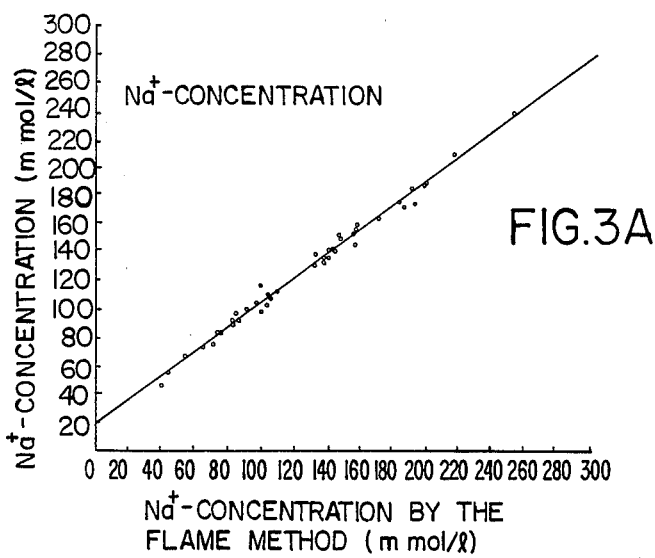
FIGS. 3A, B, C is a graph showing a correlation between a measured result by a measuring method according to the present invention and a measured result by other measuring methods, respectively, as to the meaasurement of a urine.
Figure 3B:
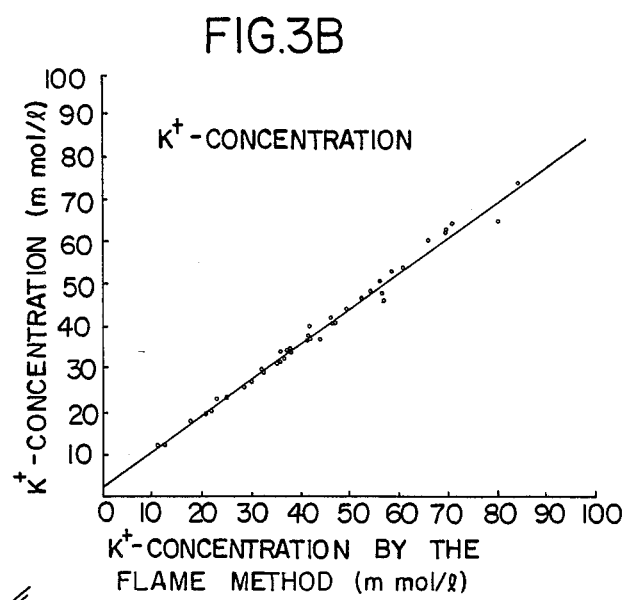
Figure 3C:
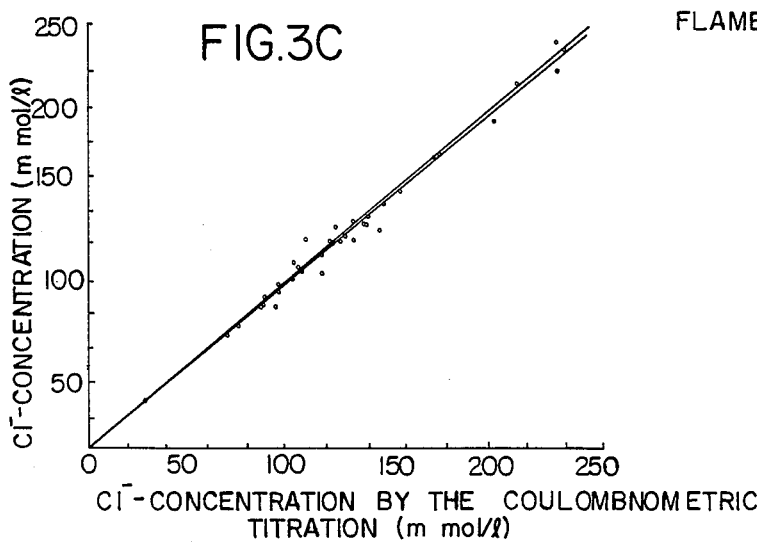
Figure 4A:
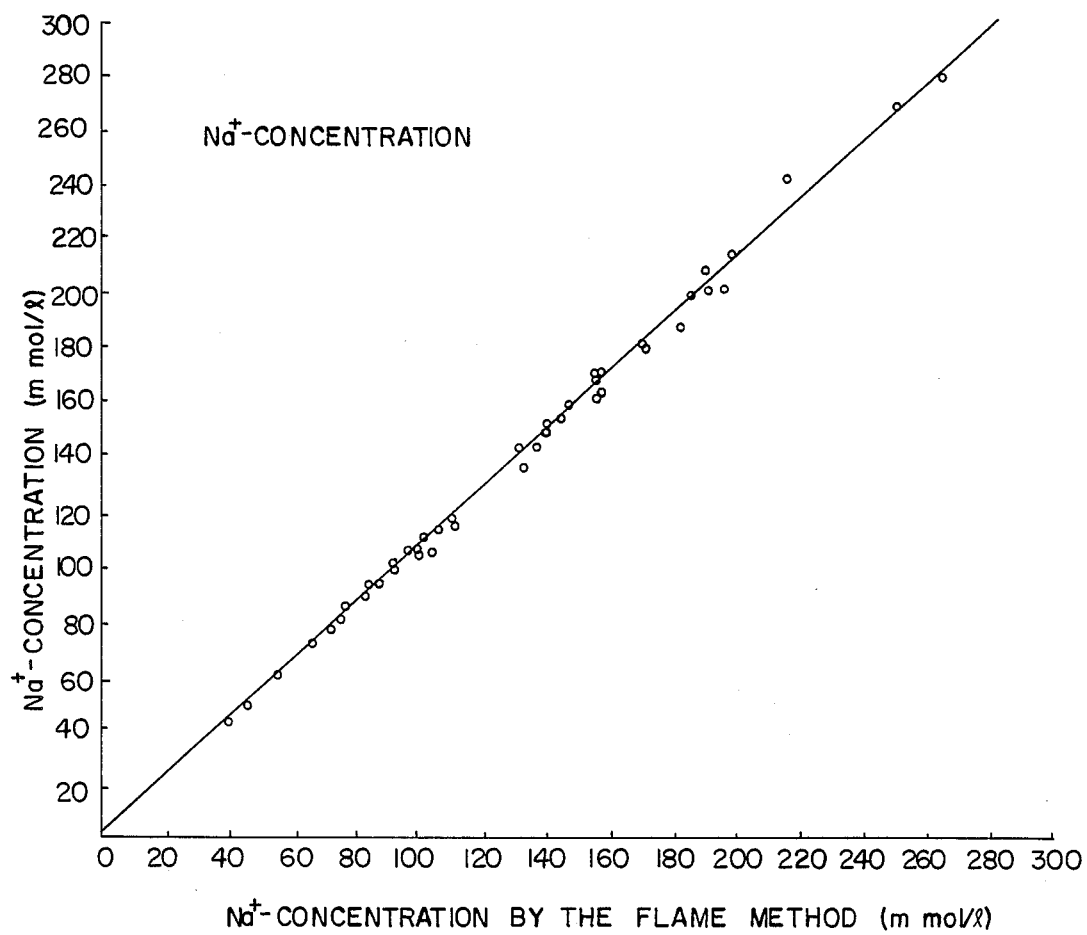
FIGS. 4A, B, C is a graph showing a correlation between a measured result by the conventional measuring method and a measured result by other measuring methods, respectively, as to the measurement of a urine.

In addition, a correlation between a measured result of a concentration of Na+, K+ and Cl− in a urine measured in said Example and by the conventional method, respectively, and a measured result of that measured by other measuring methods (Na+ and K+ are measured by the flame analysis while Cl− is measured by the coulobmnometric titration) is shown in FIGS. 3 and 4, in FIGS. 3A, B, C shows the correlation as to the measured result in said Example while FIGS. 4A, B, C shows the correlation as to the measured result by the conventional method.

As obvious from Table 1 and FIGS. 1 to 4, the Example of the present invention is superior to the conventional method in all of reproducibility, linearity and correlation with other measuring methods.

Figure 5A:
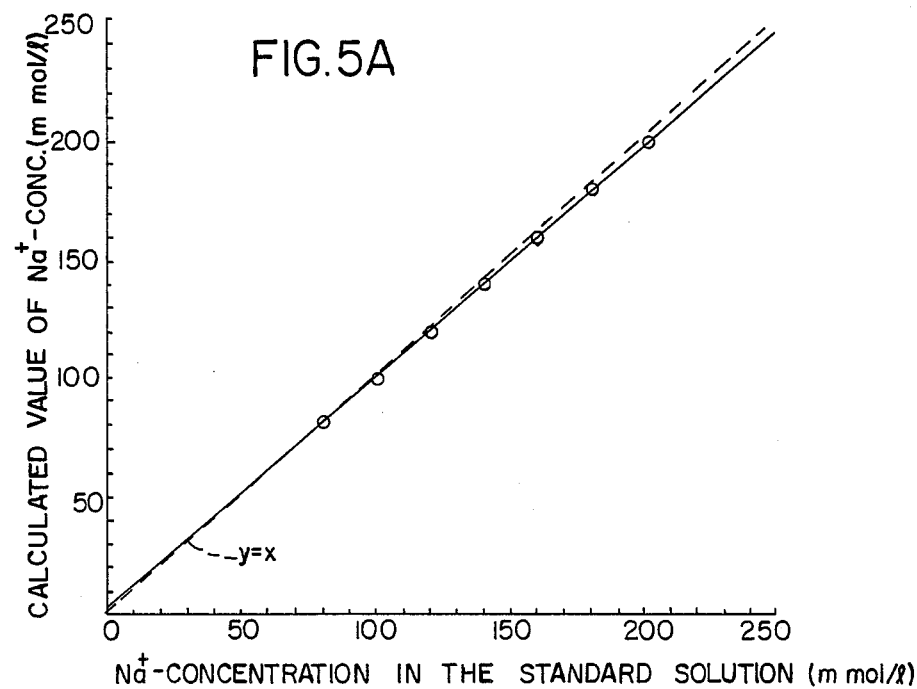
FIGS. 5A, B is a graph showing a linear a relation between
$Na^+$-concentration in a blood measured by a measuring method according to the present invention and a $Na^+$-concentration of the standard solution, and a linear a relation between
$Cl^-$-concentration in the blood measured by the measuring method according to the present invention and a $Cl^-$-concentration of the standard solution, respectively.
Figure 5B:
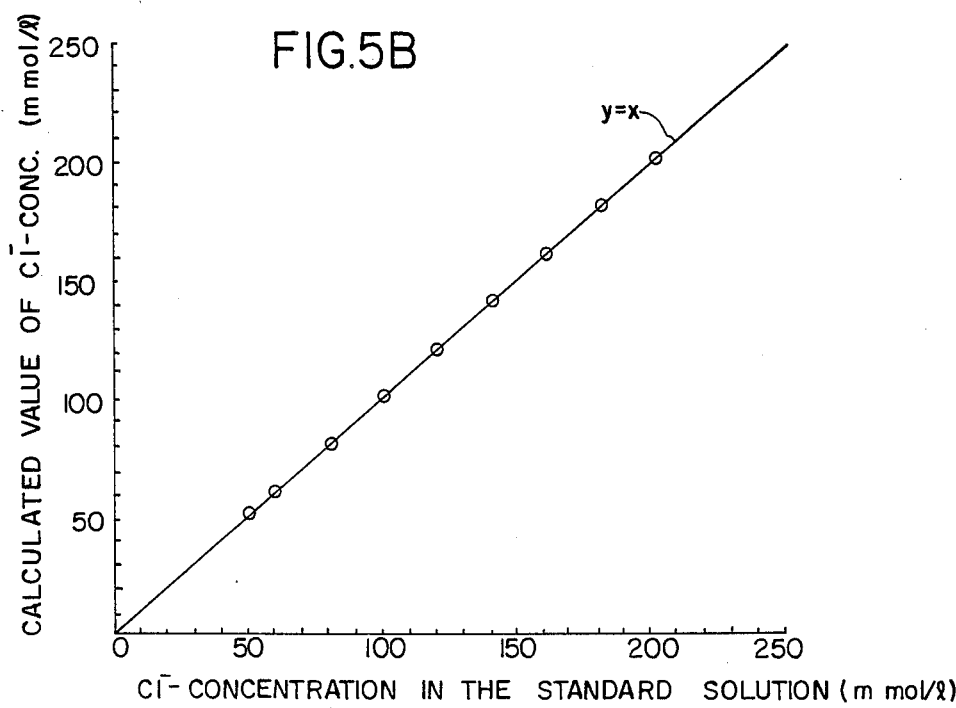
Figure 7A:
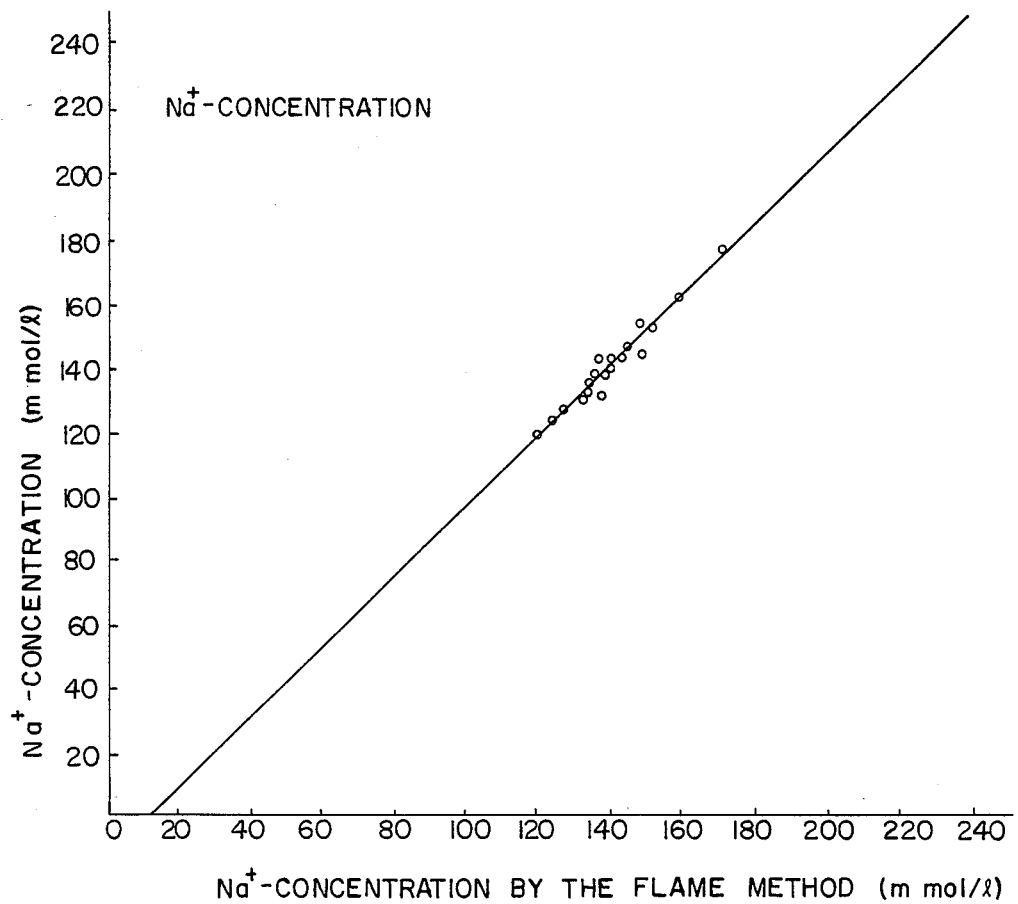
FIGS. 7A, B, C is a graph showing a correlation between a measured result by a measuring method according to the present invention and a measured result by other measuring methods, respectively, as to the measurement of a blood.
Figure 7B:
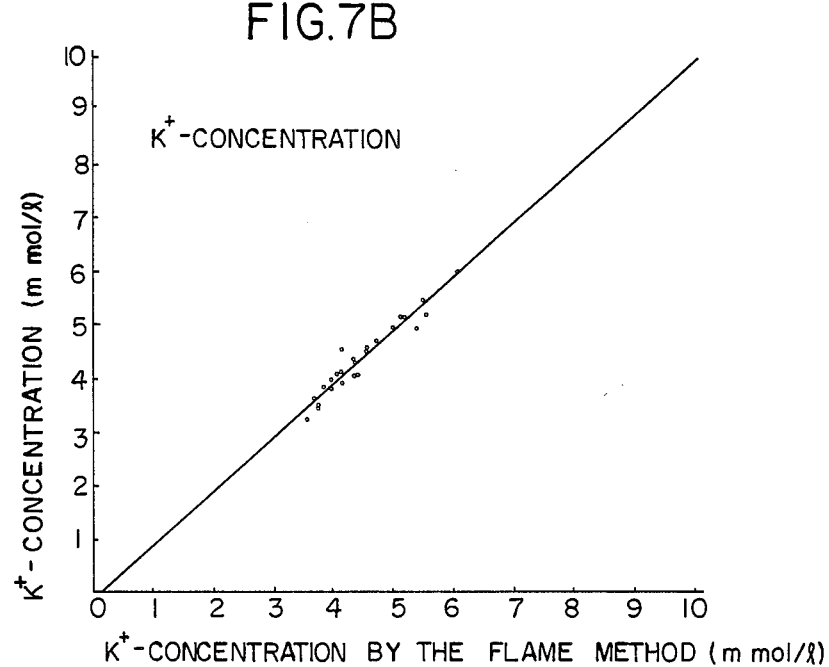
Figure 7C:
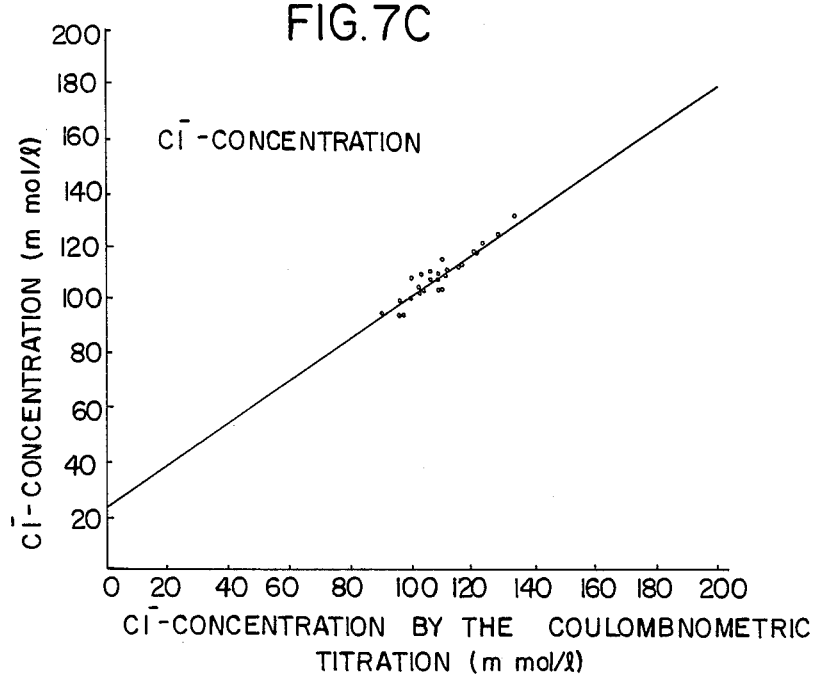
Figure 8A:
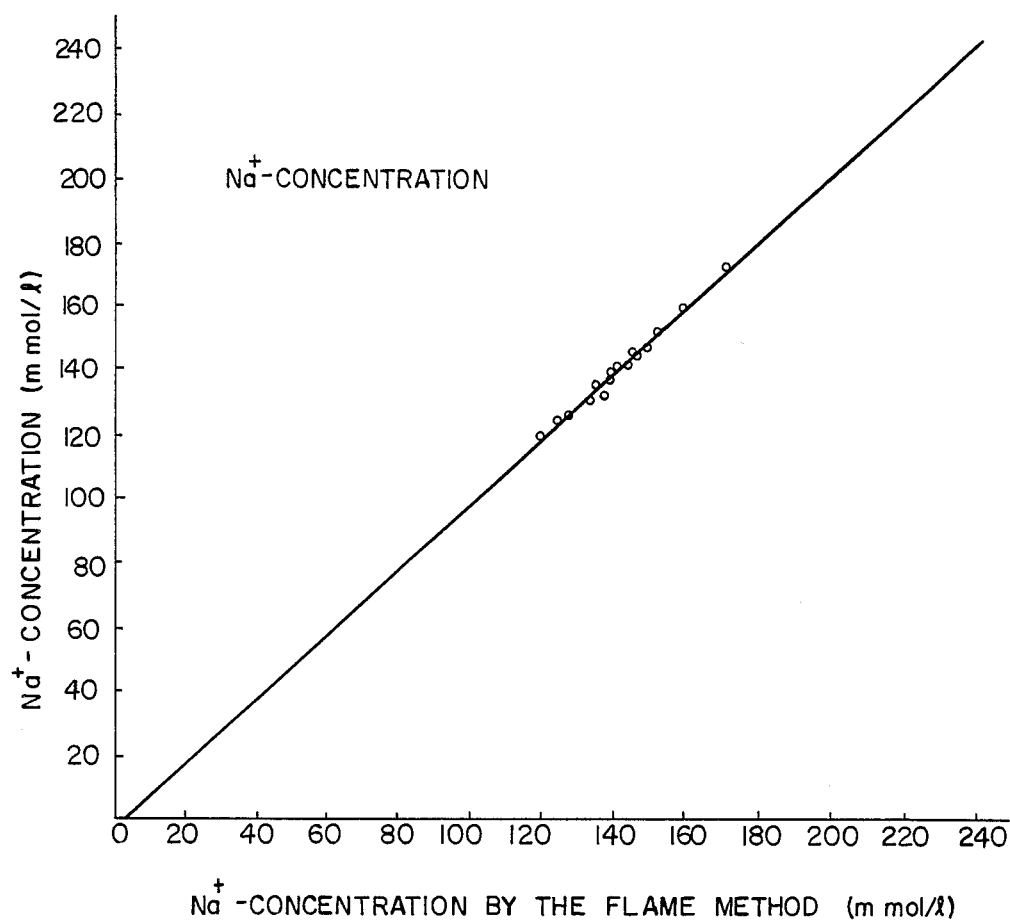
FIGS. 8A, B, C is a graph showing a correlation between a measured result by the conventional measuring method and a measured result by other measuring methods, respectively, as to the measurement of a blood.
Figure 8B:
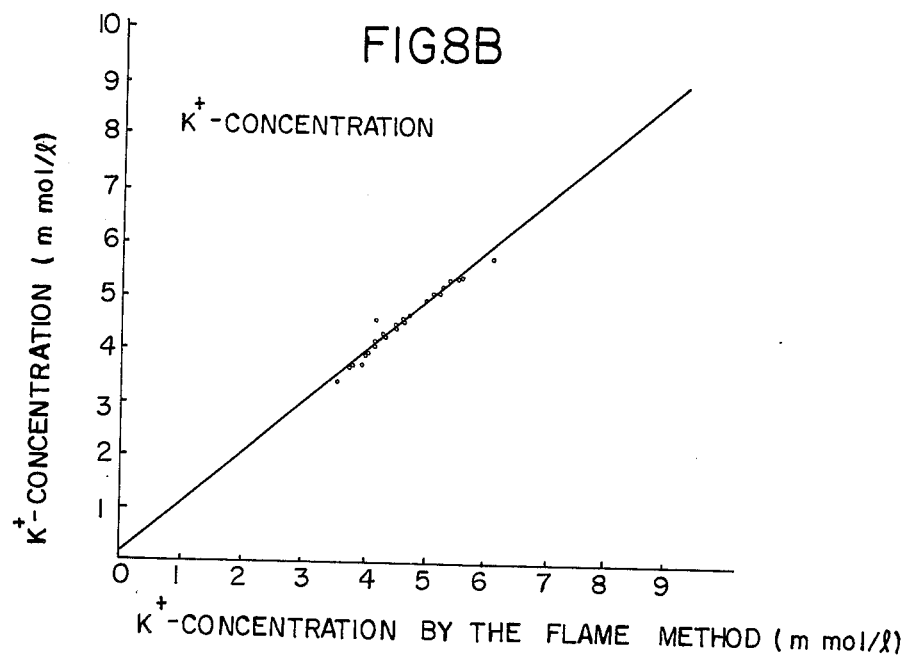
Figure 8C:
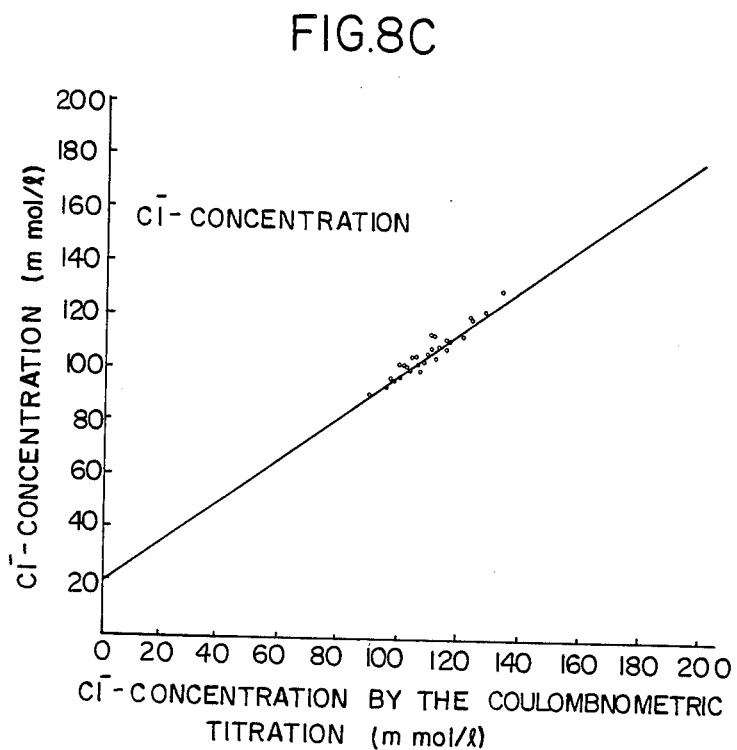

Nextly, the reproducibility of a measured result of the electrolytes in the blood measured by the use of the calibrating solution for a blood used in the measurement of the urine in said Example, and by the conventional method, is shown in Table 2 the linear relation is shown in FIGS. 5, 6 and the correlation with other measuring methods is shown in FIGS. 7, 8, in which FIGS. 5A, B and FIGS. 7A, B, C show the result relating to the Example while FIGS. 6A, B and FIGS. 8A, B, C show the result relating to the conventional method.

TABLE 2

|  |  | Na+ mmol/L | K+ mmol/L | Cl− mmol/L |
| --- | --- | --- | --- | --- |
| Example | x | 144.6 | 4.35 | 107.6 |
|  | S.D. | 0.12 | 0.007 | 0.22 |
|  | C.V. | 0.08% | 0.16% | 0.21% |
| Conventional method | x | 147.1 | 4.41 | 109.9 |
|  | S.D. | 0.62 | 0.019 | 0.58 |
|  | C.V. | 0.42% | 0.43% | 0.53% | wherein $\bar{x}$: average value; S.D.: standard deviation; C.V.: coefficient of variation As obvious from Table 2 and FIGS. 5 to 8, also in measuring blood the method according to the Example is superior to the conventional method in all of reproducibility, linearity and correlation with other measuring methods.

Although a solution of salts containing all of $Na^+$, $K^+$ and $Cl^-$ was used as the diluent for the urine in said Example, for example in the case where $Na^+$ and $Cl^-$ are objects to be measured, a diluent containing salts of $Na^+$ and $Cl^-$ is used. That is to say, the kind of salts to be added to the diluent may be determined in dependence upon the objects to be measured.

The measuring method according to the present invention can be applied also the measurement of electrolytes in body liquids other than a blood and a urine. And, since if the multiplication factor of dilution is changed while maintaining the composition of the diluent, a calculated value can be obtained by only changing the variables of computed values for the urine, a user can select the multiplication factor of dilution in dependence upon the conditions, such as quantity of the urine, if an analyzer is provided with a multiplication factor of dilution-setting portion and the like capable of optionally selecting the multiplication factor of dilution.

According to a method of measuring electrolytes in a blood and a urine by of the present invention, as above described, a calibrating solution for a blood can be used also for the measurement of the urine by diluting the urine with a diluent containing salts of ions to be measured. Therefore, troubles, such as the displacement of the calibrating solution in dependence upon a sample to be measured i.e. a blood or a urine, can be avoided all and as a result, measuring apparatus and the operation thereof can be simplified.

In addition, since the urine, which is originally measured in a remarkably wide measuring range, is measured in a narrow measuring range by diluting it with said diluent, the accuracy of measurement can be improved. In particular, an inferior linearity in a lower-concentration range and a higher-concentration range, which has been a disadvantage in the measurement by the conventional method, can be avoided, that is to say a disadvantage inherent in the conventional method also can be avoided.

What is claimed is:

1. A method of measuring a concentration of at least one electrolyte selected from the group consisting of $Na^+$, $K^+$ and $Cl^-$ in both a urine sample and a blood sample, which comprises:

preparing a calibrating solution containing at least one ion selected from the group consisting of $Na^+$ in an amount of 120 to 160 mmol/liter, $K^+$ in an amount of 4.0 to 6.0 mmol/liter and $Cl^-$ in an amount of 100 to 140 mmol/liter;

preparing a diluent containing a buffering agent and at least one ion selected from the group consisting of $Na^+$ in an amount of 50 to 150 mmol/liter, $K^+$ in an amount of 0 to 4.0 mmol/liter and $Cl^-$ in an amount of 50 to 150 mmol/liter, wherein said ions in said calibrating solution and said diluent are the same as said electrolyte to be measured;

diluting said urine sample with said diluent;

measuring said electrolyte in the diluted urine with an electrode using said calibrating solution;

calculating the concentration of said electrolyte in said urine sample based on the measured value; and measuring the concentration of said electrolyte in said blood sample with an electrode using said calibrating solution.

2. A method according to claim 1, wherein said urine sample is diluted with said diluent by a factor of 6 to 11.

3. A method according to claim 1, wherein said blood sample is whole blood, blood plasma or serum.

* * * * *